(12) United States Patent
Broaddus et al.

(10) Patent No.: US 8,226,694 B2
(45) Date of Patent: Jul. 24, 2012

(54) CLOSURE DEVICE FOR SKULL PLATES AND RELATED METHOD THEREOF

(75) Inventors: William C. Broaddus, Midlothian, VA (US); Zhi-Jian Chen, Glen Allen, VA (US); George T. Gillies, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 583 days.

(21) Appl. No.: 12/304,801

(22) PCT Filed: Jun. 26, 2007

(86) PCT No.: PCT/US2007/014881
§ 371 (c)(1),
(2), (4) Date: May 18, 2009

(87) PCT Pub. No.: WO2008/002595
PCT Pub. Date: Jan. 3, 2008

(65) Prior Publication Data
US 2010/0042158 A1 Feb. 18, 2010

Related U.S. Application Data

(60) Provisional application No. 60/816,716, filed on Jun. 27, 2006.

(51) Int. Cl.
*A61B 17/84* (2006.01)
(52) U.S. Cl. .................................................. 606/286
(58) Field of Classification Search .................. 606/280, 606/71, 283, 286, 298, 300, 303, 306, 307, 606/309, 310, 314, 74, 75, 324, 151
See application file for complete search history.

(56) References Cited

U.S. PATENT DOCUMENTS

| | | | | |
|---|---|---|---|---|
| 2,260,048 A | * | 10/1941 | Newell | 411/552 |
| 2,555,291 A | * | 5/1951 | Poupitch | 411/549 |
| 4,842,465 A | * | 6/1989 | Pease et al. | 411/337 |
| 5,800,436 A | | 9/1998 | Lerch | |
| 5,961,519 A | | 10/1999 | Bruce | |
| 6,022,351 A | | 2/2000 | Bremer | |
| 6,168,596 B1 | | 1/2001 | Wellisz | |
| 6,190,389 B1 | | 2/2001 | Wellisz | |

(Continued)

FOREIGN PATENT DOCUMENTS

DE 199 52 359 3/2001

(Continued)

OTHER PUBLICATIONS

"Craniofix" brochure, by Aesculap, 1000 Gateway Blvd. So., San Francisco, CA 94080, 1998.

(Continued)

*Primary Examiner* — Eduardo C Robert
*Assistant Examiner* — David Comstock
(74) *Attorney, Agent, or Firm* — Robert J. Decker

(57) ABSTRACT

A method and means of cranial bone flap fixation that provides, among other things, the re-opening, resetting and/or repositioning of the bone flap during neurosurgical procedures. The instrumentation central to this method and means is MR and CT-visible to aid in imaging-based localization of it. The method and means can also be used in other types of medical procedures where certain kinds of hard or firm tissue fixation is desirable according to the method of the invention.

16 Claims, 6 Drawing Sheets

U.S. PATENT DOCUMENTS

| | | |
|---|---|---|
| 6,258,091 B1 | 7/2001 | Sevrain |
| 6,270,500 B1 | 8/2001 | Lerch |
| 6,302,884 B1 | 10/2001 | Wellisz |
| 6,379,363 B1 * | 4/2002 | Herrington et al. ............. 606/79 |
| 6,485,493 B1 | 11/2002 | Bremer |
| 6,511,482 B1 | 1/2003 | Wellisz |
| 6,537,277 B2 | 3/2003 | Vom Berg |
| 6,537,286 B2 | 3/2003 | Acampora |
| 6,554,835 B1 | 4/2003 | Lee |
| 6,572,623 B1 | 6/2003 | Birchall |
| 6,582,435 B2 | 6/2003 | Wellisz |
| 6,585,739 B2 | 7/2003 | Kuras |
| 6,620,165 B2 | 9/2003 | Wellisz |
| 6,652,531 B2 | 11/2003 | Wellisz |
| 6,679,885 B2 | 1/2004 | Wellisz |
| 6,709,437 B2 | 3/2004 | Wellisz |
| 6,755,834 B2 | 6/2004 | Amis |
| 6,921,401 B2 | 7/2005 | Lerch |
| 6,923,812 B1 | 8/2005 | Wellisz |
| 7,048,737 B2 * | 5/2006 | Wellisz et al. .................. 606/70 |
| 7,048,738 B1 * | 5/2006 | Wellisz et al. .................. 606/70 |
| 7,819,907 B2 * | 10/2010 | Agbodoe ...................... 606/324 |
| 2002/0016593 A1 * | 2/2002 | Hearn et al. .................... 606/72 |
| 2002/0169455 A1 * | 11/2002 | Bannerman et al. ............ 606/99 |

FOREIGN PATENT DOCUMENTS

| | | |
|---|---|---|
| SU | 1816443 | 5/1993 |
| WO | WO 97/42912 | 11/1997 |

OTHER PUBLICATIONS

"Bioplate Biomesh" brochure, Bioplate, Inc., 3643 Lenawee Avenue, Los Angeles, CA 90016, 1998.

* cited by examiner

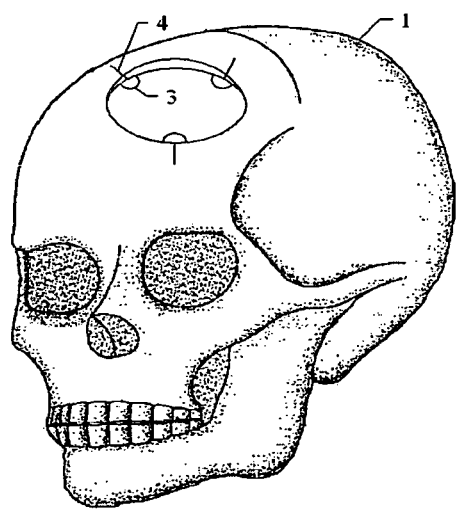
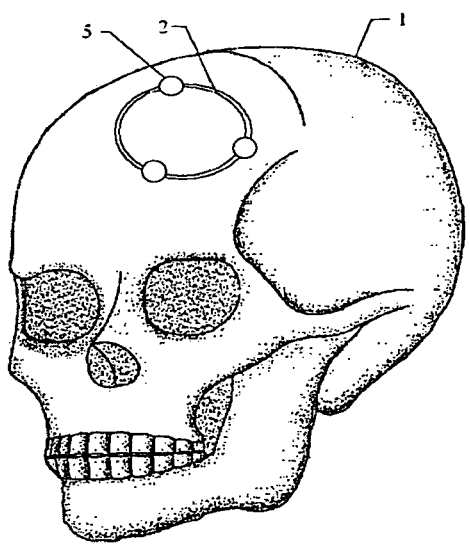
FIG. 1A FIG. 1B
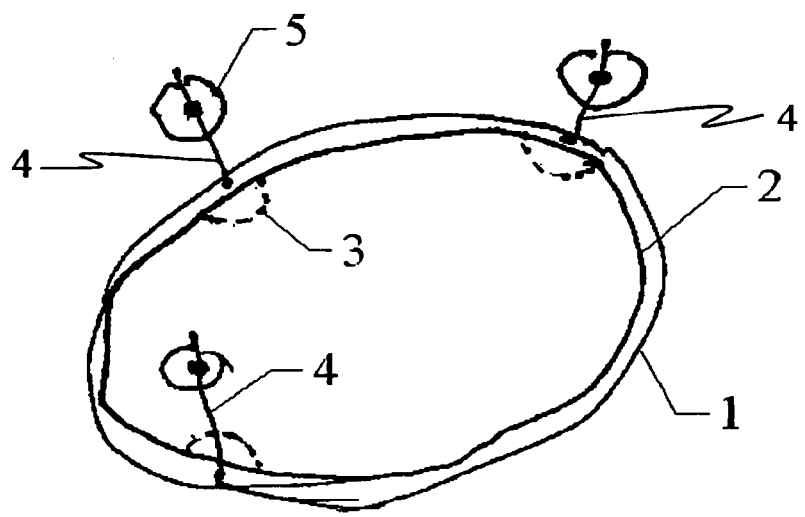
FIG. 2

CLOSURE DEVICE FOR SKULL PLATES AND RELATED METHOD THEREOF

CROSS-REFERENCE TO RELATED APPLICATIONS

The present application is a national stage filing of International Application No. PCT/US2007/014881, filed Jun. 26, 2007, which claims benefit of priority under 35 U.S.C. §119(e) from U.S. Provisional Application Ser. No. 60/816,716 filed Jun. 27, 2006, entitled "Closure Device for Skull Plates and Related Method Thereof," wherein the disclosures are hereby incorporated by reference herein in their entirety.

FIELD OF THE INVENTION

This invention relates generally to medical implants and methods used to fix excised hard tissue secondary to the repair of an injury or the completion of a surgical procedure. More specifically, this invention may be utilized for fixing cranial bone flaps in place following neurosurgical procedures.

BACKGROUND OF THE INVENTION

Bone flaps are typically reattached into an opening in the skull following a craniotomy or other type of neurosurgical operation using clips, fasteners, and various other types of interconnection instrumentation that penetrate the bone, as well as posts that couple to capture plates that can laterally position the bone flap within the aperture in the skull. A significant limitation of these methods is that they do not allow for a rapid and convenient means or method for the neurosurgeon to de-couple the capture plates, thus enabling either additional access to the brain tissues or re-adjustment of the bone flap position.

There is a need for a fastening and capture mechanism that allows for easy and effective repositioning of the capture plates during the skull closure process, especially in those cases where the surgeon decides to add additional fastening systems following placement and fixation of an initial set of fasteners and capture plates.

SUMMARY OF THE INVENTION

To overcome these and other limitations, an aspect of various embodiments of the present invention provides a method, device, and means for obtaining fixation of a bone flap within an aperture in the skull that allows for easy and effective repositioning of the bone flap. An approach disclosed herein uses sets of capture plates to laterally position the bone flap within the aperture, with a shaft intersecting each opposing pair of capture plates. The sets of capture plates may be positioned circumferentially around the outer perimeter of the bone flap, at locations deemed most appropriate by the neurosurgeon or practitioner. Flexibility intrinsic to the upper capture plate allows the interconnection shaft to be extended beyond the distal surface of the lower plate, and thus rotated into a detenting lock position or, alternatively, into a detenting unlock position for the loosening or withdrawal of the shaft and repositioning of the bone flap.

An aspect of various embodiments of the present invention provides for the use of a shaft with arms projecting from the distal end of the shaft. By rotation of the shaft, the device can be placed such that one arm is located underneath the skull and one arm located underneath the adjacent bone flap, with a capture plate then pressed down onto the shaft proximally, thus locking the system in place.

An aspect of an embodiment of the present invention provides a device for fixation of an excised piece of hard or firm tissue within an aperture in a larger hard or firm tissue region of a patient. The device comprising: a lower plate to be positioned below the excised piece of hard or firm tissue; a shaft having a distal end and a proximal end; an arm located at the distal end of the shaft, wherein the arm extends transversely from the shaft; and an aperture in the lower plate, the aperture adapted to allow passage of the shaft through the lower plate in an inward direction and when the shaft is rotated the arm rotates to a position preventing passage of the shaft through the lower plate in an outward direction.

An aspect of an embodiment of the present invention provides a device for fixation of an excised piece of hard or firm tissue within an aperture in a larger hard or firm tissue region of a patient. The device comprising: a shaft having a distal end and a proximal end; and a projection that extends transversely from the shaft, wherein for the fixation of the device at least a portion of the projection is to be located under the excised piece of hard or firm tissue and at least a portion of the projection is to be located under the larger hard or firm tissue region.

An aspect of an embodiment of the present invention provides a method for fixating an excised piece of hard or firm tissue within an aperture in a larger hard or firm tissue region of a patient. The method comprising: positioning a lower plate below the excised piece of hard or firm tissue, the lower plate having an aperture therein; providing a shaft having a distal end and a proximal end, the shaft having an arm that is located at the distal end of the shaft, wherein the arm extends transversely from the shaft; passing the shaft through the lower plate in an inward direction; rotating the shaft; and preventing passage of the shaft through the lower plate in an outward direction.

An aspect of an embodiment of the present invention provides a method for fixating an excised piece of hard or firm tissue within an aperture in a larger hard or firm tissue region of a patient. The method comprising: providing a shaft having a distal end and a proximal end; the shaft having a projection that extends transversely from the shaft; and locating at least a portion of the projection under the excised piece of hard or firm tissue and at least a portion of the projection under the larger hard or firm tissue region.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

FIGS. 1(A) and 1(B) are schematic perspective views of a bone flap fixated within an aperture in the skull using devices in accordance with an embodiment of the present invention.

FIG. 2 is a schematic view of general and non-limiting exemplary configurations for positioning and use of the devices in fixation of a bone flap in the skull.

DETAILED DESCRIPTION OF THE INVENTION

Figure 3:
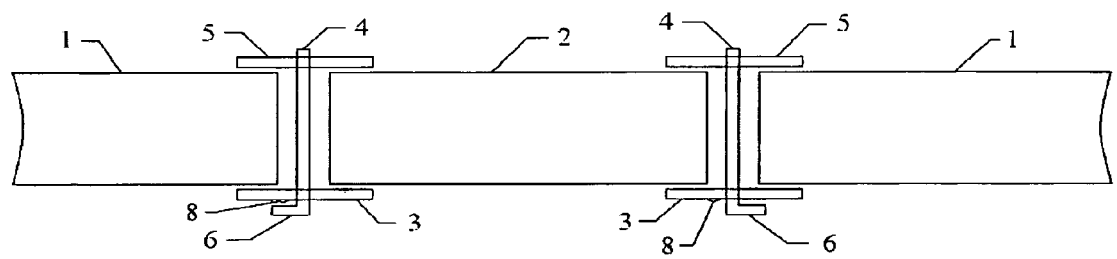
FIG. 3 is a schematic elevational view of a bone flap positioned within an aperture using two plates and a shaft.

FIG. 1(A) shows a schematic view of a section of the skull 1 from which a circular bone flap 2 has been cut out to/y be any variety of shapes, but a circular shape is shown in order to simplify the illustration of the concept. An embodiment of the invention, consisting of a lower plate 3 and a shaft 4, is placed at various locations within the aperture in the skull 1. The shaft 4 is shown as inserted before the bone flap 2 is inserted into the aperture in the skull 1, but can also be inserted after the bone flap 2 is inserted. FIG. 1B shows a schematic view of the bone flap 2 positioned in the desired location within the aperture in the skull 1. An upper plate 5 is positioned above the bone flap 2 and in communication with the shaft 4 in order to secure the bone flap 2 within the skull 1. The upper plate 5 may be attached to the shaft 4 before or after passage of the shaft 4 through the lower plate 3. The upper plate 5 may be retained against the bone flap 2 and/or the skull 1 by nut, rivet, clip, pin, adhesive, or any other means of attachment.

FIG. 2 shows a schematic view of an embodiment of the invention positioned around the bone flap 2. The lower plate 3 is located below the bone flap 2 in communication with the shaft 4. The upper plate 5 is in the process of being slid over the shaft 4, and then will be retained against the bone flap 2 to secure positioning in the skull 1 (i.e. hard or firm tissue). The shaft 4 may then be severed.

FIG. 3 shows a schematic cross-sectional view of a bone flap 2 that has been cut out of a skull 1 (i.e. hard or firm tissue) to allow the neurosurgeon access to the dural and subdural regions of the cranium. Following the neurosurgical procedure, the bone flap 2 is positioned within the aperture created in the skull 1 by use of an upper plate 5 and lower plate 3 which are then mechanically coupled together by a shaft 4. The shaft 4 has an arm 6 located at its distal end, or the end nearest to the lower plate 3. The arm 6 extends transversely from the shaft 4 and is located under the lower plate 3 to hold the lower 3 and upper plate 5 together. At least one protrusion 8 is shown on the distal end of the lower plate 3 to aid in securing the shaft 4. The protrusions 8 can be placed at various locations on the lower plate 3. The arm 6 is shown extending substantially at a right angle from the shaft 4. The angle of the arm 6 may vary just as long as one or more arms or segments of arms can be located under the lower plate 3 in such a way as to achieve fixation.

Figure 4:
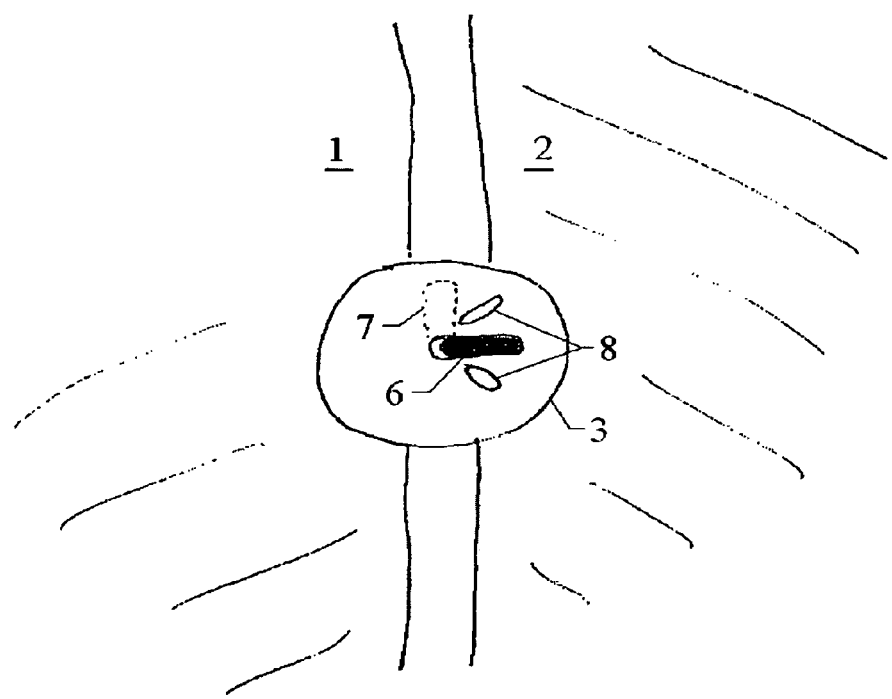
FIG. 4 is a schematic distal plan view of the lower plate, with the arm of the shaft positioned between two protrusions.

FIG. 4 shows a schematic plan view of the distal end of the lower plate 3 as seen looking outward from the surface of the brain. The lower plate has an aperture 7 through which the shaft 4 may be slid during assembly and fixation of the upper 5 and lower plate 3. The aperture 7 is a size and shape that will permit passage of the arm 6 that extends from the distal end of the shaft 4. Upon appropriate placement of the fixation system, the surgeon may rotate the shaft 4 relative to the upper plate 5 until passage of the shaft 4 back through the lower plate 3 is prevented in order to hold the bone flap 2 firmly in place within the aperture in the skull 1. The distal end of the lower plate is shown with two protrusions 8, for example detents, in which the shaft 4 is passed over one detent 8 and secured between the two protrusions 8. It should be appreciated that the protrusions or detents can be any retention mechanism or means for retaining the shaft 4 or arms in place. The upper plate may contain elasticity or flexibility to allow a downward force on the shaft 4 to cause the arm 6 to clear the protrusion 8 when the shaft 4 is rotated.

The shaft 4 and the upper 5 and lower plate 3 may be made of radio-opaque, CT-visible and/or MR-visible and compatible materials to facilitate imaging-based localization of them, as might be required during radiological studies associated with the neurosurgical procedure, which are either pre- or post-procedure.

It should be appreciated that the invention can also be utilized for any hard or firm tissue region in the body, for example skull, sternum, other desired locations of the body anatomy, or when skull bones are still soft and thus a firm tissue, as in children. Additionally, the natural hard tissue, firm tissue or bone flap can be replaced with artificial material.

Figure 5:
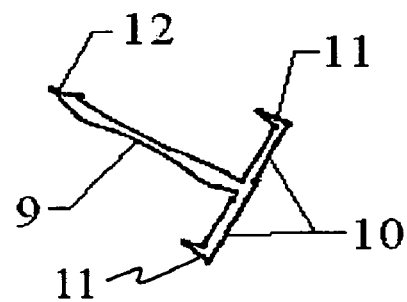
FIG. 5 is a schematic perspective view of the shaft and two extending arms.

FIG. 5 shows a schematic perspective view of an embodiment of the invention comprising a shaft 9 and a projection consisting of one or more arms 10. The arms 10 have pedestals that taper to a point 11 and the shaft 9 tapers at its end to a point 12, although the end need not be a point and may be blunt or a variety of contours. Pedestals 11 may be constructed to break off or grind down in height when shearing force is applied by rotating the shaft 9, which allows for easy removal and/or adjustment of the invention. The number of arms, segments of arms, and the angle of the segments and arms may vary as long as one or more arms or segments of arms can be located under a portion of the bone flap 2 and under a portion of the skull 1 (i.e. hard or firm tissue).

Figure 6:
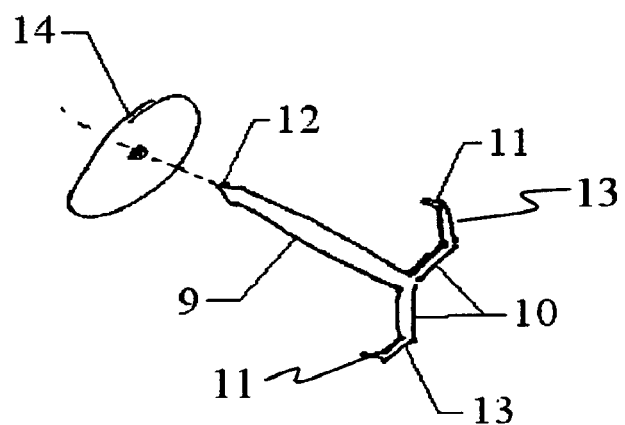
FIG. 6 is a schematic perspective view of the shaft and two extending angled arms and shown with an exploded view of a corresponding upper plate.

FIG. 6 shows a schematic perspective view of an embodiment of the invention comprising a shaft 9 and a projection consisting of one or more arms 13. The arms 13 are angled to provide spring-like restoring force to aid in achieving fixation of the bone flap 2 within the skull 1. The two arms have pedestals that taper to a point 11. An upper plate 14 may be positioned above the bone flap and/or skull and in communication with the shaft to secure the device. Pedestals 11 may be constructed to break off or grind down in height when shearing force is applied by rotating the shaft 9, which allows for easy removal and/or adjustment of the invention. The number of arms, segments of arms, and the angle of the segments and arms may vary as long as one or more arms or segments of arms can be located under a portion of the bone flap 2 and under a portion of the skull 1 (i.e. hard or firm tissue).

Figure 7:
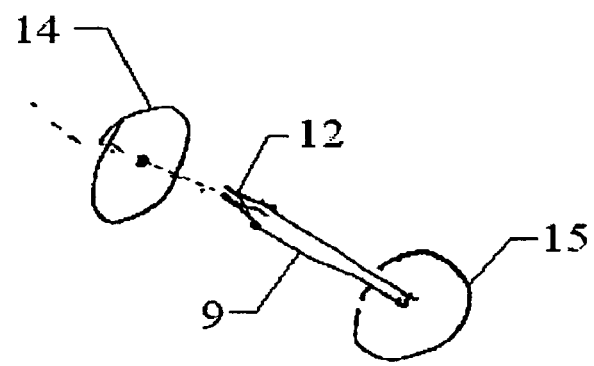
FIG. 7 is a schematic perspective view of the shaft and a continuous plate and shown with an exploded view of a corresponding upper plate.
Figures 8A, 8B, 8C, 8D:
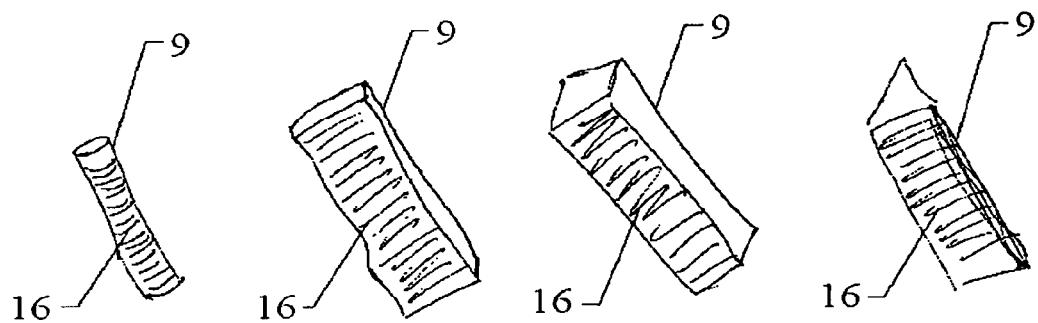
FIGS. 8(A)-(D) provide schematic perspective views of the shaft having circular, rectangular, square and triangular cross-sections, respectively.

FIG. 7 shows a schematic perspective view of an embodiment of the invention comprising a shaft 9 and a projection consisting of a continuous plate 15. It should be appreciated that continuous generally refers to general surface area and may have partial segments omitted or apertures therein. The configuration of the continuous plate 15 may vary as long as one or more portions of the plate can be located under a portion of the bone flap 2 and under a portion of the skull 1.

FIGS. 8(A)-(D) show schematic perspective views of examples of possible geometrical configurations of the shaft 9 cross-section, including but not limited to a circle, rectangular, square, or triangle, respectively. Also shown are the striations/serrations 16 on the shaft 9, similar to those on a cable tie, to further aid in achieving fixation. It should be appreciated that the shape, size, contour, and axis of the shaft, as well as the curvature and angles of the shaft, may vary as required or desired.

Figure 9:
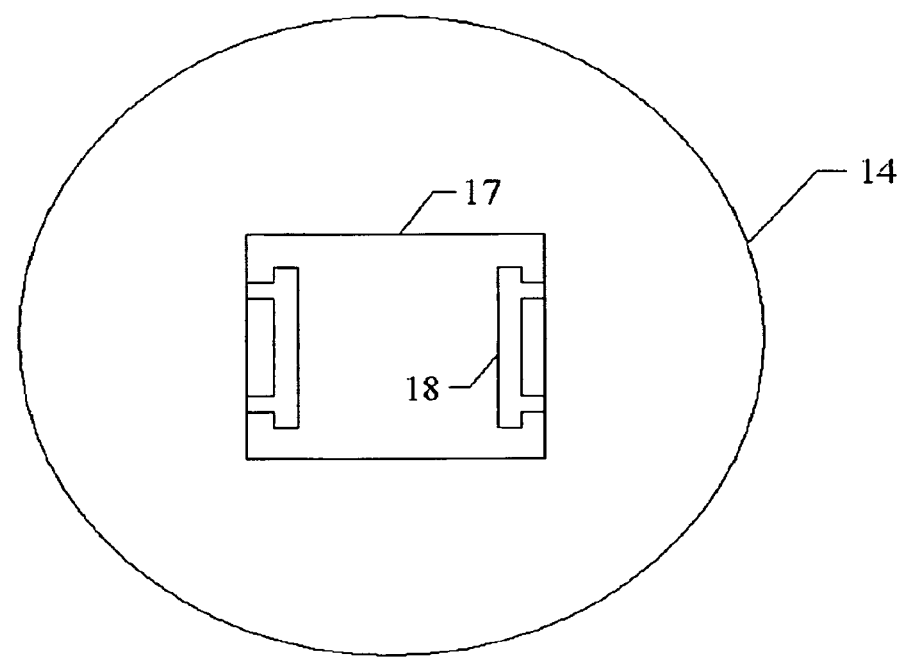
FIG. 9 is a top plan schematic view of the upper plate and aperture therein with ratcheting teeth.

FIG. 9 shows a schematic plan view of the upper plate 14 and an aperture 17 therein with ratcheting teeth 18 used for fixation of the shaft (not shown).

Figure 10:
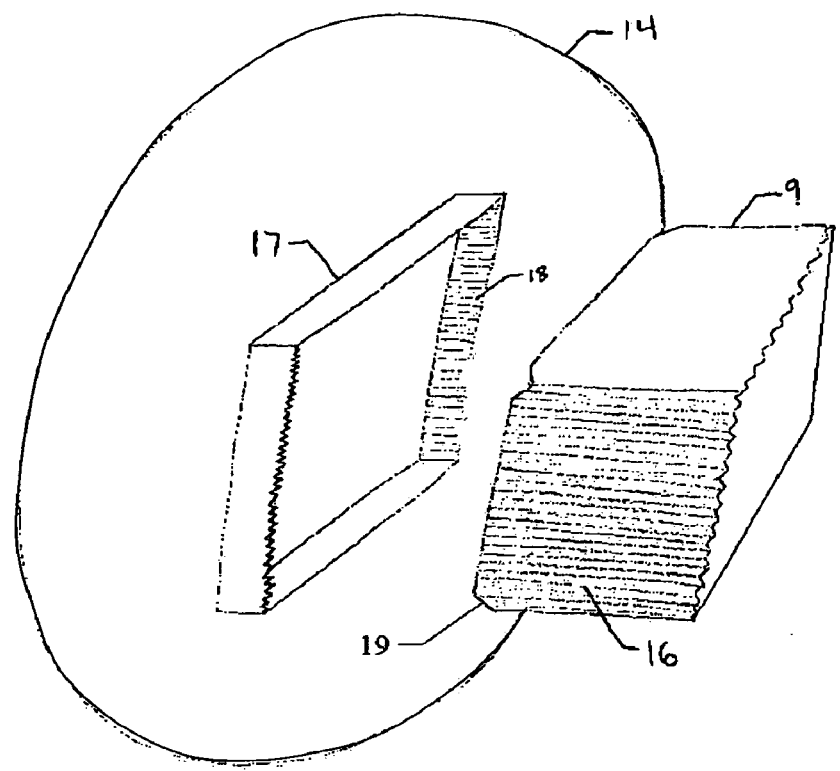
FIG. 10 is a schematic perspective view of the upper plate in the process of being mounted on the shaft, with the upper plate having an aperture for receiving the shaft shown in FIG. 8C, for example.

FIG. 10 shows a schematic perspective view of the upper plate 14 adjacent to and about to be mounted onto the proximal end of the shaft 9. The shaft 9 may have chamfered corners 19 to facilitate the relative rotation of the upper plate 14 around the axis of the shaft 9, in order to achieve alignment of the ratcheting teeth 18 on the upper plate 14 with the striations/serrations 16 on the shaft 9.

Figure 11:
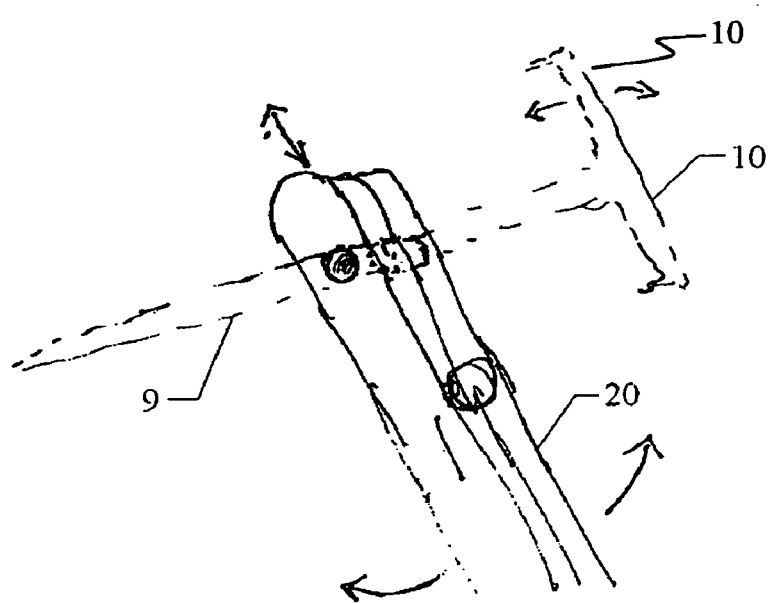
FIG. 11 is a schematic perspective view of the adjustment tool needed to rotate a shaft (shown with dashed lines) having a round cross section.

FIG. 11 shows a schematic perspective view of the general configuration of the pliers-like implement 20 used to grab and hold the shaft 9 (shown in dotted lines) of an embodiment of the invention having a circular cross section.

Figure 12:
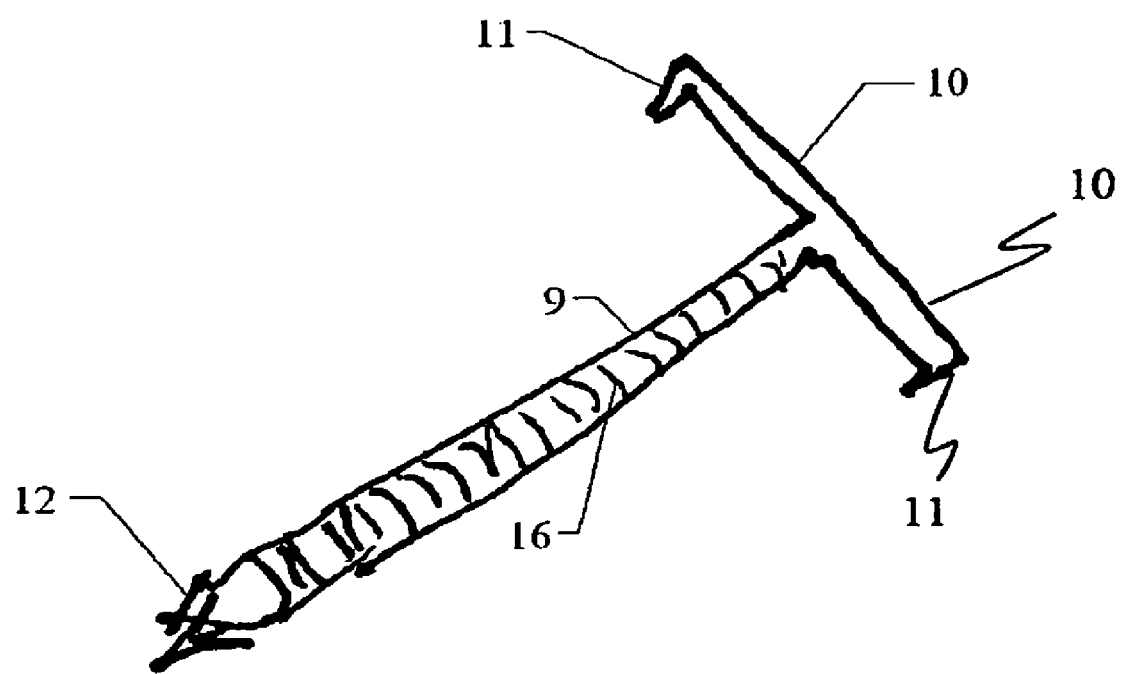
FIG. 12 is a schematic perspective view of the embodiment in FIG. 5 shown with striations/serrations on the shaft that that may be utilized in FIG. 11, for example.

FIG. 12 shows a schematic perspective view of an embodiment of the invention as similarly shown in FIG. 5, for example, having striations/serrations 16 on the shaft 9 as shown.

It should be noted that the shaft 9, arms 10 and 11, continuous plate 15, and upper plate 14 (or any related components) may be made of radio-opaque, CT-visible and/or MR-visible and compatible materials to facilitate imaging-based localization of them, as might be required during radiological studies associated with the neurosurgical procedure, which are either pre-, intra-, or post-procedure.

It should be noted that the shaft, arms, pedestals, plates, protrusions, apertures, and continuous plate, (or any related components of the device and method) may have more than one unit and a variety of sizes, flexibility, elasticity, rigidity, contours, dimensions, and materials as desired and required in spirit with the embodiments disclosed and discussed herein.

It should be appreciated that the invention can also be utilized for any hard or firm tissue region in the body, for example skull, sternum, other desired locations of the body anatomy, or when skull bones are still soft and thus a firm tissue, as in children. Additionally, the natural hard tissue, firm tissue or bone flap can be replaced with artificial material.

The composition, devices, systems and methods of various embodiments of the invention disclosed herein may utilize aspects disclosed in the following U.S. Patents, foreign patents, and publications are hereby incorporated by reference herein in their entirety:

U.S. Patent Documents

| 7,048,738 | May 2006 | Wellisz et al | 606/70 |
| 7,048,737 | May 2006 | Wellisz et al | 606/70 |
| 6,923,812 | August 2005 | Wellisz | 606/72 |
| 6,921,401 | July 2005 | Lerch et al | 606/72 |
| 6,755,834 | June 2004 | Amis | 606/72 |
| 6,709,437 | March 2004 | Wellisz | 606/71 |
| 6,679,885 | January 2004 | Wellisz | 606/72 |
| 6,652,531 | November 2003 | Wellisz et al | 606/72 |
| 6,620,165 | September 2003 | Wellisz | 606/69 |

-continued

| 6,585,739 | July 2003 | Kuras et al | 606/72 |
| 6,582,435 | June 2003 | Wellisz et al | 606/72 |
| 6,572,623 | June 2003 | Birchall et al | 606/76 |
| 6,554,835 | April 2003 | Lee | 606/72 |
| 6,537,286 | March 2003 | Acampora et al | 606/151 |
| 6,537,277 | March 2003 | Vom Berg et al | 606/71 |
| 6,511,482 | January 2003 | Wellisz et al | 606/69 |
| 6,485,493 | November 2002 | Bremer | 606/70 |
| 6,379,363 | April 2002 | Herrington et al | 606/79 |
| 6,302,884 | October 2001 | Wellisz et al | 606/69 |
| 6,270,500 | August 2001 | Lerch | 606/72 |
| 6,258,091 | July 2001 | Sevrain et al | 606/72 |
| 6,190,389 | February 2001 | Wellisz et al | 606/69 |
| 6,168,596 | January 2001 | Wellisz et al | 606/69 |
| 6,022,351 | February 2000 | Bremer et al | 606/72 |
| 5,961,519 | October 1999 | Bruce et al | 606/69 |

Foreign Patent Documents

| 1816443 | May 1993 | (SU) | 606/69 |
| WO 97/42912 | November 1997 | (WO) | |
| DE 199 52 359 | March 2001 | (DE) | |

Other Publications

"Craniofix" brochure, by Aesculap, 1000 Gateway Blvd. So., San Francisco, Calif. 94080, 1998.

"Bioplate Biomesh" brochure, Bioplate, Inc., 3643 Lenawee Avenue, Los Angeles, Calif. 90016, 1998.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A device for fixation of an excised piece of hard or firm tissue within an aperture in a larger hard or firm tissue region of a patient, said device comprising:
   a lower plate to be positioned below the excised piece of hard or firm tissue;
   a shaft having a distal end and a proximal end;
   an arm located at said distal end of said shaft, wherein said arm extends transversely from said shaft;
   an aperture in said lower plate, said aperture adapted to allow passage of said shaft through said lower plate in an inward direction and when said shaft is rotated said arm rotates to a position preventing passage of said shaft through said lower plate in an outward direction; and
   an upper plate to be positioned above the excised piece of hard or firm tissue and in communication with said shaft, wherein said upper plate is configured to be slid over said shaft and retained against the excised piece of hard or firm tissue and/or the larger hard tissue region for fixation of the excised piece of hard or firm tissue within the aperture in the larger hard or firm tissue region of the patient.

2. The device of claim 1, wherein said arm extends substantially at a right angle from said shaft.

3. The device of claim 1, wherein at least one protrusion is located on said distal side of said lower plate and which said arm of said shaft can be passed over and secured.

4. The device of claim 3, wherein said protrusion is a detent.

5. The device of claim 4, wherein there are at least two said detents located on said distal side of said lower plate and said arm of said shaft can be passed over and secured between said detents.

6. The device of claim 3, wherein said protrusion is a raised surface.

7. The device of claim 3, wherein there are at least two said protrusions located on said distal side of said lower plate and said arm of said shaft can be passed over and secured between said protrusions.

8. The device of claim 1, wherein there is more than one said aperture in said lower plate and/or more than one said arm to facilitate the locking and unlocking of said device by the surgeon.

9. The device of claim 1, wherein said device is radio-opaque, MR-visible and compatible, and/or CT-visible for radiological purposes.

10. The device of claim 1, wherein the hard or firm tissue is a skull or sternum of a patient.

11. The device of claim 1, wherein said upper plate is elastic or flexible enough to allow a downward force on said shaft to cause said arm of said shaft to clear at least one said protrusion when said shaft is rotated.

12. The device of claim 1, wherein said upper plate is attached to said proximal end of said shaft before passage of said shaft through said lower plate.

13. The device of claim 1, wherein said upper plate is separate from said shaft and may be attached to said plate after passage of said shaft through said lower plate.

14. The device of claim 1, wherein said upper plate is retained by at least one of the following: nut, rivet, clip, pin, or adhesive.

15. A method for fixating an excised piece of hard or firm tissue within an aperture in a larger hard or firm tissue region of a patient, said method comprising:
   positioning a lower plate below the excised piece of hard or firm tissue, said lower plate having an aperture therein;
   providing a shaft having a distal end and a proximal end, said shaft having an arm that is located at said distal end of said shaft, wherein said arm extends transversely from said shaft;
   passing said shaft through said lower plate in an inward direction;
   rotating said shaft; and
   preventing passage of said shaft through said lower plate in an outward direction.

16. The method of claim 15, further comprising positioning an upper plate above the excised bone or firm tissue and in communication with said shaft.

* * * * *